US011439583B2

(12) United States Patent
Briand et al.

(10) Patent No.: US 11,439,583 B2
(45) Date of Patent: Sep. 13, 2022

(54) PROTECTIVE SKIN COMPOSITIONS

(71) Applicant: AMANTIN EXPERTS, Paris (FR)

(72) Inventors: Elisabeth Briand, Gentilly (FR);
Jean-Baptiste Dumas Milne Edwards,
Paris (FR); Jacques Delort, Paris (FR)

(73) Assignee: AMANTIN EXPERTS, Paris (FR)

( * ) Notice: Subject to any disclaimer, the term of this patent is extended or adjusted under 35 U.S.C. 154(b) by 98 days.

(21) Appl. No.: 15/501,782

(22) PCT Filed: Aug. 5, 2014

(86) PCT No.: PCT/EP2014/066848
§ 371 (c)(1),
(2) Date: Feb. 3, 2017

(87) PCT Pub. No.: WO2016/019981
PCT Pub. Date: Feb. 11, 2016

(65) Prior Publication Data
US 2017/0224603 A1 Aug. 10, 2017

(51) Int. Cl.
*A61K 8/81* (2006.01)
*A61K 8/73* (2006.01)
*A61Q 17/00* (2006.01)
*A61K 8/19* (2006.01)
*A61K 9/00* (2006.01)
*A61K 47/32* (2006.01)
*A61K 9/06* (2006.01)
*A61K 31/78* (2006.01)
*A61K 33/10* (2006.01)
*A61K 31/731* (2006.01)
*A61K 31/734* (2006.01)
*A61K 8/02* (2006.01)
*A62D 5/00* (2006.01)
*G21F 1/10* (2006.01)
*G21F 3/02* (2006.01)

(52) U.S. Cl.
CPC ............ *A61K 8/817* (2013.01); *A61K 8/0204* (2013.01); *A61K 8/19* (2013.01); *A61K 8/73* (2013.01); *A61K 8/731* (2013.01); *A61K 8/733* (2013.01); *A61K 8/8147* (2013.01); *A61K 8/8158* (2013.01); *A61K 9/0014* (2013.01); *A61K 9/06* (2013.01); *A61K 31/731* (2013.01); *A61K 31/734* (2013.01); *A61K 31/78* (2013.01); *A61K 33/10* (2013.01); *A61K 47/32* (2013.01); *A61Q 17/00* (2013.01); *A62D 5/00* (2013.01); *G21F 1/10* (2013.01); *G21F 3/02* (2013.01); *A61K 2800/72* (2013.01); *A61K 2800/75* (2013.01)

(58) Field of Classification Search
None
See application file for complete search history.

(56) References Cited

U.S. PATENT DOCUMENTS

| 2004/0166128 | A1* | 8/2004 | Noel | A61K 8/06 424/401 |
| 2008/0038219 | A1* | 2/2008 | Mosbaugh | A61K 8/19 424/74 |
| 2012/0258151 | A1* | 10/2012 | Li | A61K 8/27 424/401 |
| 2012/0321573 | A1* | 12/2012 | Karp | A61K 9/0014 424/59 |

FOREIGN PATENT DOCUMENTS

| DE | 19802539 | A1 | 7/1999 | |
| EP | 0661047 | A1 * | 7/1995 | A61K 8/11 |
| EP | 1459736 | A1 | 9/2004 | |
| WO | 9826788 | A1 | 6/1998 | |
| WO | 2004041235 | A1 | 5/2004 | |
| WO | 2012098546 | A2 | 7/2012 | |

OTHER PUBLICATIONS

Fullerton, Contact Dermatitis, 32, 1995 (Year: 1995).*
Phyllosilicates. Nelson, Stephen A. Mineralogy, Tulane University, Aug. 18, 2015 (Year: 2015).*
Fevola, Cosmetics & Toiletries, 2013 (Year: 2013).*
International Search Report, dated Aug. 24, 2015 in related International Application No. PCT/EP2014/066848, filed Aug. 5, 2014, 7 pages.
Written Opinion of the International Searching Authority, dated Aug. 24, 2015 in related International Application No. PCT/EP2014/066848, filed Aug. 5, 2014, 13 pages.
International Preliminary Report on Patentability, dated Feb. 7, 2017 in related International Application No. PCT/EP2014/066848, filed Aug. 5, 2014, 14 pages.
Gawkrodger, D. J., et al. "The prevention of nickel contact dermatitis. A review of the use of binding agents and barrier creams." Contact Dermatitis, vol. 32, No. 5, Jan. 1, 1995, pp. 257-265.
Van Ketel, W.G., et al. "The possible chelating effect of sodium diethyldithiocarbamate (DDC) in nickel allergic patients. Patch test procedures with nickel on DDC pretreated skin." Derm Beruf Umwelt., 30(6): 198-202, 1982, Abstract Only.
Wohrl, S., et al. "A cream containing the chelator DTPA (diethylenetriaminepenta-acetic acid) can prevent contact allergic reactions to metals." Contact Dermatitis, vol. 44, No. 4, Apr. 1, 2001, pp. 224-228.

* cited by examiner

*Primary Examiner* — Susan T Tran
*Assistant Examiner* — William Craigo
(74) *Attorney, Agent, or Firm* — Christensen O'Connor Johnson Kindness PLLC

(57) ABSTRACT

The subject of the present invention is cosmetic or pharmaceutical compositions which are protective against common skin irritants or allergens. The invention is also directed to the use of these compositions to protect skin from the effects of metal. Another object of the invention is a method of preventing or protecting the skin from the effects of metal, using the compositions of the invention.

11 Claims, 6 Drawing Sheets

|  | Sample 1a | Sample 1b | Sample 2a | Sample 2b |
|---|---|---|---|---|
| Formula A Pellet |  |  |  |  |
| Formula A Supernatant |  |  |  |  |
| Formula B Pellet |  |  |  |  |
| Formula B Supernatant |  |  |  |  |

|  | Test 1 | Test 2 | Test 3 |
|---|---|---|---|
| Composition C pellet |  |  |  |
| Composition C Supernatant |  |  |  |
| Composition D pellet |  |  |  |
| Composition D supernatant |  |  |  |

| | Test 1 | Test 2 | Test 3 |
|---|---|---|---|
| Composition A |  |  |  |
| Composition B |  |  |  |
| Composition C |  |  |  |
| Composition D |  |  |  |
| Composition E |  |  |  |

| Sample | DMG detection |
|---|---|
| Composition A |  |
| Composition B |  |
| Composition C |  |
| Composition D |  |

PROTECTIVE SKIN COMPOSITIONS

TECHNICAL FIELD

The subject of the present invention is cosmetic or pharmaceutical compositions which are protective against common skin irritants or allergens.

The invention also relates to the use of these compositions to protect skin from the effects of metal.

Another object of the invention is a method of preventing or protecting the skin from the effects of metals, using the compositions of the invention.

BACKGROUND

A lot of people are allergic or develop skin reactions such as contact dermatitis while in contact with items containing irritants (such as jewelries, watches, jean button, buckle, coins . . . ). In particular, nickel allergy is one of the most common causes of allergic contact dermatitis. Nickel allergy is commonly associated with earrings and other jewelry, particularly jewelry associated with body piercings. But nickel can be found in many everyday items, from coins to zippers, from cellphones to eyeglass frames.

Nickel, cobalt and chromium are common allergens that can induce contact allergies. They also have irritant properties. Epidemiology studies have shown that the sensitization toward nickel evolves to allergic contact dermatitis if exposure exceeds the individual threshold. Numerous studies have been published to determine the prevalence of these contact dermatitis due to metal exposure. A recent review (Thyssen. J. P., et al., Contact Dermatitis 2007: 57: pp 287-299) has analyzed the prevalence of contact allergy in the general population based on studies conducted mainly in North America and Western Europe between 1966 and 2007. The most prevalent allergen was nickel, with a medium prevalence of 8.6%. This study concluded that "nickel was an important cause of contact allergy in the general population and it was widespread in both men and women. [ . . . ] pierced ears were a significant risk factor for nickel allergy. Nickel was a risk factor for hand eczema in women." The evaluation of the influence of the limitation to nickel exposure has been recently published by the same group (Thyssen. J. P., Contact Dermatitis, Volume 65, Issue Supplement s1, pp 1-68, September 2011). It was concluded that environmental nickel exposure was the most important factor to develop contact allergy toward nickel.

A common strategy to protect people sensitive to metal is to add varnish to make a protective layer between the irritating or allergenic object and the exposed skin. Some varnishes are specifically advised as a protective layer toward nickel (such as nickel Guard™ sold by Allergy Asthma Technology or Isoclip sold by Tradiphar) but common nail varnish is often used instead. However, the use of varnish is not a cosmetically acceptable solution to put directly on the skin. Moreover, the use of varnish itself is suspected to be a cause of initial sensitization of people toward nail varnish (Ozkaya. E., and A. Ekinci. Clin Exp Dermatol. 2010 June; 35(4): pp 37-40).

Most of the products claiming an efficiency for this application are cosmetic or dermatological products containing a significant amount of occlusive ingredients, preferably issued from petrol derivatives, such as vaseline and dimethicone, that act as an isolating but non-specific layer between the skin and the irritating items. These products deposit an hydrophobic and occlusive film on the skin that would reduce the penetration into skin of irritating or allergenic molecules while the film is intact. However, these compounds are known to potentially alter the integrity of the skin and be themselves the cause of skin irritations or rashes, either due to their own allergenic or irritant potential, or as a consequence of the barrier film that they form at the surface of the skin. Moreover, these barriers creams are not efficient, as illustrated by the prevalence of contact dermatitis in skin diseases.

The strategies advised to people suffering from skin reaction toward metal irritants or allergens exposure are indeed either avoidance of contact with the irritating or allergenic items or treatment of the rashes triggered by these metals. No specific products to protect the skin for people suffering from contact dermatitis nor to protect people from risk of developing allergies due to metal irritants or allergens is yet available.

None of the existing methods aimed to protect the skin against contact with nickel or other metals is suitable for a cosmetic or pharmaceutical composition. Indeed, this kind of composition should give a good feel, must be compatible with skin pH on a daily use and offer an optimal efficiency.

The use of calcium carbonate particles to prevent contact dermatitis due to nickel exposure has been disclosed (US 2012/0321573). However, the use of such ingredients in cosmetic preparations induces several problems. Mainly, the introduction of calcium carbonate or other salt carbonates in a oil in water emulsion would raise the pH well above skin pH. Skin pH is indeed usually comprised between 5.5 and 6.5, while a suspension of calcium carbonate in water at atmospheric $CO_2$ pressure would raise aqueous pH at 9.7-9.8, which could induce irritation to skin, specially for people suffering from high skin sensitivity. Increasing skin pH could also help the development of bacteria that are usually inhibited by the acidic pH environment on normal skin (Koting H. C., et al., Clin Investig, 1993; 71(8): pp 644-648).

Second, the calcium carbonate would require a complex formulation to be incorporated in stable cosmetic or pharmaceutical products. None of these aspects are taken into account to develop products that can efficiently protect skin against metal exposure.

Most importantly, $CaCO_3$ and other carbonates would partly dissociate at a pH 4-8 required for a topical product (Coto, B., et al., Fluid Phase Equilibria. 324 (2012) pp 1-'7), allowing free carbonates to chelate metals and bring them through skin, thereby limiting the possible effects of the $CaCO_3$ particles.

Usually, the absorption of compounds applied to skin is limited by the stratum corneum, which forms a very structured barrier at the surface of the skin. The passage of molecules through the cornified layer of the skin takes place at a very low diffusion rate and it is known that beads having a size greater than 10 nm remain at the surface of the skin (Rolland A., et al., 1993. Pharm Res 10: pp 1738-1744). However, these $CaCO_3$ molecules, once soluble, are able to bind nickel ions and these complexes are small enough to penetrate epidermis.

SUMMARY

The applicant surprisingly and unexpectedly found that specific ingredients recognized by the CIR (Cosmetic International Review), and bearing carboxylic acid, sulfonic acid or sulfate groups are useful to specifically protect the skin toward irritant or allergenic metals.

The applicant indeed found that specific metal capturing agents bearing carboxyl, sulfonyl or sulfate moieties combine the ability to effectively capture metals such as nickel and to remain at the surface of the skin at physiological pH, and are suitable for use in cosmetic or pharmaceutical preparations.

A subject of the invention is also a method to avoid contact with metal irritants or allergens using these metal capturing agents.

Another subject of the invention is the use of these metal capturing agents to reduce skin exposure to metal irritants or allergens coming from the environment.

Another subject of the invention is the use of these metal capturing agents to reduced skin exposure to radioactive isotopes in potentially contaminated environments.

Other subject-matters, characteristics, aspects and advantages of the invention will become even more clearly apparent on reading the description, examples and figures which follow.

DETAILED DESCRIPTION

Figure 1:
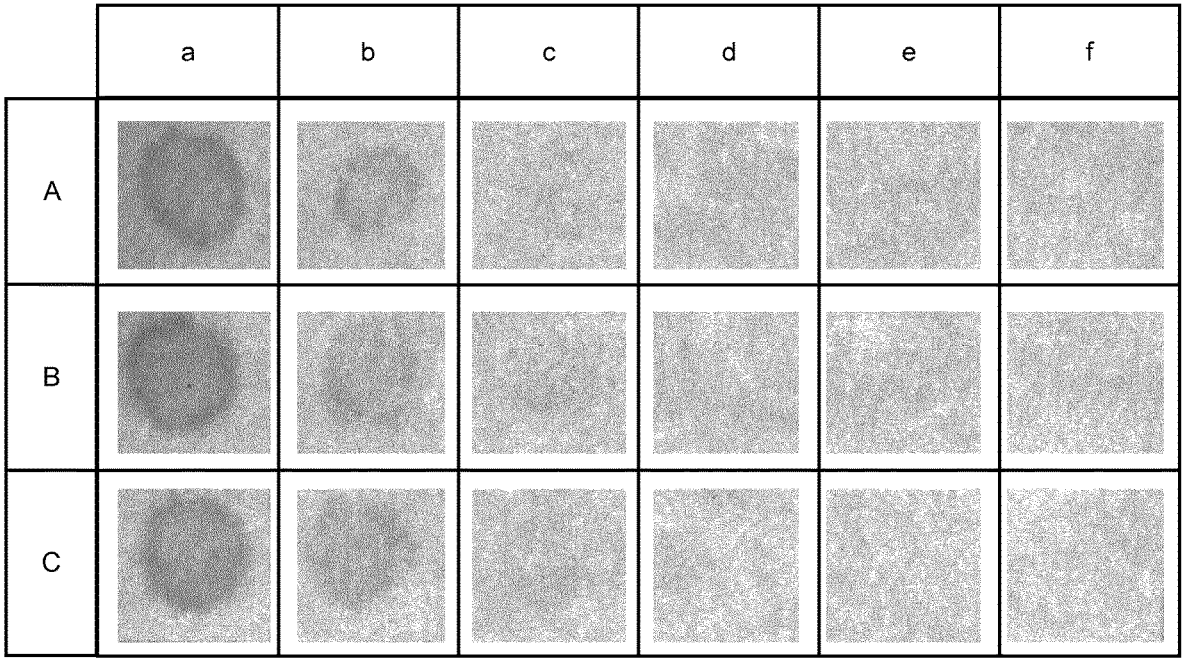
FIG. 1: Nickel in aqueous solutions at various concentrations, revealed by DMG in presence of the compositions to be tested. Stock nickel solution concentration was 1 mg/mL, and dilutions tested were 1:2 (500 µg/mL) (lane a), 1:4 (250 µg/mL) (lane b), 1:8 (125 µg/mL) (lane c), 1:16 (62.5 µg/mL) (lane d), 1:32 (31.25 µg/mL) (lane e) and 1:64 (15.65 µg/mL) (lane f).

The present invention is directed to a composition to protect skin against contact with metal irritants and allergens that comprises, in a cosmetically acceptable medium, at least one metal capturing agent bearing carboxyl, sulfonyl or sulfate moieties and that does not dissociate at pH 4 to 8.

Within the meaning of the present invention, the terms "at least one" means one or more and thus includes single compounds as well as mixtures.

The metal capturing agents of the present invention are useful toward skin exposure to cations in general, since the carboxyl, sulfonyl and sulfate groups would capture these cations, without being limited to nickel, cobalt, chromium, zinc or lead.

These agents could also limit skin exposure toward other metal cations that could become an asset due increasing exposure through environment.

Preferably, the agent bearing carboxyl, sulfonyl or sulfate moieties is chosen among polyacrylic acid polymer and its derivatives, polysaccharide from i) gum of microbial origin, such as xanthan gum or gellan gum ii) gum of algae origin, such as carrageenan, in particular iota carrageenan, kappa carrageenan or alginate, iii) polysaccharide from animal origin, such as chitosan, iv) polysaccharide from vegetal origin, such as cellulose derivative polymer, pectine and its derivatives. Such metal capturing agents are typically found in the aqueous phase of a composition.

Among polyacrylic acid polymers, one can find
a) synthetic hydrophilic polymers that comprise a free carboxylic acid moieties, such as polymer of acrylic acid known as carbomer, crosslinked homopolymers of acrylic acid, copolymers of acrylic acid, carboxyvinyl polymers, acrylic acid/polyallyl sucrose polymers, polyacrylic compounds and acrylic acid/ethyl acrylate copolymer.
b) synthetic hydrophilic polymers that comprise a sulfonic acid moiety, such as homopolymers of acrylamidopropanesulfonic acid, crosslinked homopolymers of acrylamidopropanesulfonic acid, copolymers of acrylamidopropanesulfonic acid The agent bearing carboxyl moieties is a homopolymer or heteropolymer bearing at least one free carboxylic acid moiety per monomer. the agent bearing carboxyl moieties is preferably chosen among carbomer, carboxyvinyl polymers, acrylic acid/polyallyl sucrose polymers, polyacrylic compounds and acrylic acid/ethyl acrylate copolymer and polyacrylamidopropanesulfonic acid. Preference is particularly given, among the carboxyl bearing agents to carbomer or carboxymethyl cellulose.

The agent bearing sulfonyl moieties is a homopolymer or heteropolymer bearing at least one free sulfonyl moiety per monomer. Preferably, the agent bearing sulfonyl moieties is chosen among homopolymers of acrylamidopropanesulfonic acid, crosslinked homopolymers of acrylamidopropanesulfonic acid and copolymers of acrylamidopropanesulfonic acid.

The agent bearing sulfate moieties is a homopolymer or heteropolymer bearing at least one free sulfate acid moiety per monomer. Preferably, the sulfate bearing agent agent is a natural sulfated polysaccharide.

Sulfate moieties has a chemical structures that enable the binding of sodium and calcium ions, a property which is used in industry to stabilize emulsion by gelling it using such polymer. A well-known class of this gelling agent is carrageenans (MacArtain, P., et al., Carbohydrate Polymers, 2003, 53 (4), pp 395-400) known as a food additive in European Union under the E number E407 (or E407a). For these polymers, kappa-carrageenans and iota-carrageenan are able to form gels in presence of cationic ions. More preferably, the polysaccharide present in the compositions of the invention is chosen among carrageenans, and even more preferably among iota carrageenans.

The compositions of the invention are able to protect skin against contact with metal irritants or allergens. These metal irritants or allergens may be polyvalent metal cations, and preferably nickel, cobalt or chromium. However, other metals can be captured by these polymers. It can be, as example, $Ag+$, $Au+$, $Tl+$, $Hg+$, $Cs+$, $Ti2+$, $Zn2+$, $Ni2+$, $Pd2+$; $Cd2+$, $Pt2+$, $Hg2+$, $T13+$, $Cr3+$, $Co3+$, $Cu+$, $Cu2+$, $Cu3+$, $Pb2+$, $Pb3+$, $Fe3+$, $La3+$, $In3+$, $Ga3+$, $Sr3+$, $Al3+$, $U3+$, $U4+$.

According to the invention, the metal capturing agent is contained in the compositions of the invention in proportions from 0.1% to 40%, and preferably from 0.3% to 30% of the total weight of the composition.

The compositions of the invention may contain emollients that can be, without being limitative:
a) hydrocarbon based plant oil with a high triglyceride content consisting of fatty acid ester of glycerol. The fatty acid may have various chains lengths, and these chains can also be linear or branched and saturated or unsaturated. This plant oil can be avocado oil, apricot kernel oil, blackcurrant seed oil, borage seed oil, camelina seed oil, castor oil, chaulmoogra oil, corn oil, cottonseed oil, cucumber seed oil, grapeseed oil, hemp seed oil, Inca inchi oil, karite butter, millet oil, musk rose oil, olive oil, passion flower oil, perilla seed oil, rapeseed oil, sunflower oil, sweet almond oil, wheat germ oil.

b) synthetic oils or ester of formula R1COOR2 with R1 and R2 representing a linear or a branched fatty acid residues. It can be Behenyl Beeswax, Behenyl Behenate, Behenyl Erucate, Behenyl Isostearate Behenyl Olivate, Behenyl/Isostearyl Beeswax, Butyl Avocadate, Butyl Babassuate, Butyl Isostearate, Butyl Myristate, Butyl Oleate, Butyl Stearate, Butyloctyl Beeswax, Butyloctyl Behenate, Butyloctyl Candelillate, Butyloctyl Cetearate, Butyloctyl Oleate, Butyloctyl Palmitate, C10-40 Isoalkyl Acid Octyldodecanol Esters, C14-30 Alkyl Beeswax, C16-36 Alkyl Stearate, C18-38 Alkyl Beeswax, C18-38 Alkyl C24-54 Acid Ester, C20-40 Alkyl Behenate, C20-40 Alkyl Stearate, C30-50 Alkyl Beeswax, C30-50 Alkyl Stearate, C32-36 Isoalkyl Stearate, C40-60 Alkyl Stearate, C4-5 Isoalkyl Cocoate, Caprylyl Butyrate, Caprylyl Caprylate, Caprylyl Eicosenoate, Cetearyl Behenate, Cetearyl Candelillate, Cetearyl Isononanoate, Cetearyl Nonanoate, Cetearyl Olivate, Cetearyl Palmate, Cetearyl Palmitate, Cetearyl Rice Branate, Cetearyl Stearate, Cetyl Babassuate, Cetyl Behenate, Cetyl Caprate, Cetyl Caprylate, Cetyl Dimethyloctanoate, Cetyl Esters, Cetyl Isononanoate, Cetyl Laurate, Cetyl Myristate, Cetyl Myristoleate, Cetyl Oleate, Cetyl Palmitate, Cetyl Ricinoleate, Cetyl Stearate, Cetyl Tallowate, Chimyl Isostearate, Chimyl Stearate, Coco-Caprylate, Coco-Caprylate/Caprate, Coco-Rapeseedate, Decyl Castorate, Decyl Cocoate, Decyl Isostearate, Decyl Jojobate, Decyl Laurate, Decyl Myristate, Decyl Oleate, Decyl Olivate, Decyl Palmitate, Decyltetradecyl Cetearate, Erucyl Arachidate, Erucyl Erucate, Erucyl Oleate, Ethylhexyl Adipate/Palmitate/Stearate, Ethylhexyl C10-40 Isoalkyl Acidate, Ethylhexyl Cocoate, Ethylhexyl Hydroxystearate, Ethylhexyl Isononanoate, Ethylhexyl Isopalmitate, Ethylhexyl Isostearate, Ethylhexyl Laurate, Ethylhexyl Myristate, Ethylhexyl Neopentanoate, Ethylhexyl Oleate, Ethylhexyl Olivate, Ethylhexyl Palmitate, Ethylhexyl Pelargonate, Ethylhexyl Stearate, Heptyl Undecylenate, Heptylundecyl Hydroxystearate, Hexyl Isostearate, Hexyl Laurate, Hexyldecyl Hexyldecanoate, Hexyldecyl Isostearate, Hexyldecyl Laurate, Hexyldecyl Oleate, Hexyldecyl Palmitate, Hexyldecyl Stearate, Hexyldodecyl/Octyldecyl Hydroxystearate, Hydrogenated Castor Oil Behenyl Esters, Hydrogenated Castor Oil Cetyl Esters, Hydrogenated Castor Oil Stearyl Esters, Hydrogenated Ethylhexyl Olivate, Hydrogenated Ethylhexyl Sesamate, Hydrogenated Isocetyl Olivate, Hydrogenated Isopropyl Jojobate, Hydroxycetyl Isostearate, Hydroxyoctacosanyl Hydroxystearate, Isoamyl Laurate, Isobutyl Myristate, Isobutyl Palmitate, Isobutyl Perlargonate, Isobutyl Stearate, Isobutyl Tallowate, Isocetyl Behenate, Isocetyl Isodecanoate, Isocetyl Isostearate, Isocetyl Laurate, Isocetyl Myri state, Isocetyl Palmitate, Isocetyl Stearate, Isodecyl Cocoate, Isodecyl Hydroxystearate, Isodecyl Isononanoate, Isodecyl Laurate, Isodecyl Myristate, Isodecyl Neopentanoate, Isodecyl Oleate, Isodecyl Palmitate, Isodecyl Stearate, Isohexyl Caprate, Isohexyl Laurate, Isohexyl Neopentanoate, Isohexyl Palmitate, Isolauryl Behenate, Isononyl Isononanoate, Isooctyl Caprylate/Caprate, Isooctyl Tallate, Isopropyl Arachidate, Isopropyl Avocadate, Isopropyl Babassuate, Isopropyl Behenate, Isopropyl Hydroxystearate, Isopropyl Isostearate, Isopropyl Jojobate, Isopropyl Laurate, Isopropyl Linoleate, Isopropyl Myristate, Isopropyl Oleate, Isopropyl Palmitate, Isopropyl Ricinoleate, Isopropyl Stearate, Isopropyl Tallowate, Isostearyl Avocadate, Isostearyl Behenate, Isostearyl Erucate, Isostearyl Hydroxystearate, Isostearyl Isononanoate, Isostearyl Isostearate, Isostearyl Laurate, Isostearyl Linoleate, Isostearyl Myristate, Isostearyl Neopentanoate, Isostearyl Palmitate, Isotridecyl Isononanoate, Isotridecyl Laurate, Isotridecyl Myristate, Isotridecyl Stearate, Lauryl Behenate, Lauryl Cocoate, Lauryl Isostearate, Lauryl Laurate, Lauryl Myristate, Lauryl Oleate, Lauryl Palmitate, Lauryl Stearate, Lignoceryl Erucate, Myristyl Isostearate, Myristyl Laurate, Myristyl Myristate, Myristyl Neopentanoate, Myristyl Stearate, Octyldecyl Oleate, Octyldodecyl Avocadoate, Octyldodecyl Beeswax, Octyldodecyl Behenate, Octyldodecyl Cocoate, Octyldodecyl Erucate, Octyldodecyl Hydroxystearate, Octyldodecyl Isostearate, Octyldodecyl Meadowfoamate, Octyldodecyl Myristate, Octyldodecyl Neodecanoate, Octyldodecyl Neopentanoate, Octyldodecyl Octyldodecanoate, Octyldodecyl Oleate, Octyldodecyl Olivate, Octyldodecyl Ricinoleate, Octyldodecyl Safflowerate, Octyldodecyl Stearate, Oleyl Arachidate, Oleyl Erucate, Oleyl Linoleate, Oleyl Myristate, Oleyl Oleate, Oleyl Stearate, Propylheptyl Caprylate, Stearyl Beeswax, Stearyl Behenate, Stearyl Caprylate, Stearyl Erucate, Stearyl Heptanoate, Stearyl Linoleate, Stearyl Olivate, Stearyl Palmitate, Stearyl Stearate, Tetradecyleicosyl Stearate, Tetradecyloctadecyl Behenate, Tetradecyloctadecyl Hexyldecanoate, Tetradecyloctadecyl Myristate, Tetradecyloctadecyl Stearate, Tetradecylpropionates, Tridecyl Behenate, Tridecyl Cocoate, Tridecyl Erucate, Tridecyl Isononanoate, Tridecyl Laurate, Tridecyl Myristate, Tridecyl Neopentanoate, Tridecyl Stearate.

The emollient part is of from 3% to 60%, preferably from 10% to 30%.

Other ingredients can be added. The ingredient can be a non-ionic_surfactant like oxyethylated amphiphile molecules from formula R3-(O—CH2-CH2)n-OH where R3 represents a linear saturated or unsaturated alkyl chain comprising 8 to 30 carbon atoms and n is comprised between 1 and 50. Alternatively, the non-ionic surfactant can be a fatty alcohol from formula R4-OH where R4 represents a linear or branched, saturated or unsaturated alkyl chain comprising 8 to 30 carbon atoms. The non-ionic surfactant can also comprise polyoxyethylene of sorbitan esters or a poloxamer.

When present, the surfactant part is from 1 to 20%, preferably from 3 to 7%.

In one embodiment, mineral particles can be added to the composition of the invention. The possible mineral particles are nanoparticles or microparticles which present properties of binding metal irritant.

Preferably, they are selected from the group comprising zeolite, phyllosilicates, especially kaolin, potassium alum, hydroxyapatite, calcium carbonate, calcium phosphate, ammonium calcium silicate, microporous aluminosilicate, sodium alumniosilicate, calcium silicate, sodium calcium aluminosilicate, magnesium carbonates, magnesium silicate, tricalcium silicate, potassium bisulfite, potassium metabisulfite, sodium bisulfite, sodium metabisulfite, sodium sulfite, ferric orthophosphate, ferric phosphate, ferric pyrophosphate, ferric sodium pyrophosphate, magnesium sulfate, magnesium phosphate, manganese sulfate, manganese oxide, manganese carbonate, aluminum potassium sulfate, aluminum sodium sulfate, sodium aluminum phosphate, sodium bicarbonate, ammonium carbonate, ammonium sulfate, ammonium phosphate.

More preferably, they are selected from the group comprising kaolin, hydroxyapatite, potassium alum, zeolite and calcium carbonate.

When the compositions of the invention contain mineral particles, the amount incorporated in the composition is of from 5% to 40%, preferably between 10% to 25%.

The composition according to the invention is preferably aqueous and then comprises water at a concentration preferably ranging from 5% to 60% by weight, with respect to the total weight of the composition.

In a preferred embodiment of the present invention, the protecting composition of the invention contains 0.1 to 10% of polymeric metal capturing agent and 5% to 30% of emollient. In a more preferred embodiment, the protecting composition of the invention contains 0.1 to 10% of polymeric metal capturing agent, 5% to 30% of emollient and 3% to 40% of metal capturing mineral particles.

Occlusive ingredient such as silicone may be added to the composition of the invention to act as a barrier layer in addition to the capturing polymeric agent.

It may be desirable to employ humecting ingredients to improve the hydrating properties of the cosmetic products. Humecting ingredients can be glycerin, urea, hyaluronic acid and its salts, or pantolactone.

According to the invention, the composition of the present invention may also include other ingredients such as preservatives, actives ingredients used to treat skin or hair, sunscreens, dye, pigments and other co-solvants. Mention may be made to synthetic ether of glycol, that may be used as co-solvants.

A person skilled in the art will take care to choose these optional additives and their amounts so that they do not harm the properties of the compositions of the present invention.

For a cosmetic or pharmaceutical product to be acceptable, it has to sustain stability tests. As defined herein, stability is tested by placing the composition in an oven for 4 to 8 weeks at 40-45° C. and at room temperature (typically between 20° C. and 25° C.) over the same period of time. In this test, the sample is inspected regularly over the experiment time to determine the appearance of abnormalities such as oxidation (through change of color), phase segregation or change of pH. A composition is considered stable if over this period of time, no abnormality has been registered that could tamper the efficiency or degrade the cosmeticity of the product. The compositions of the invention have been tested, are stable and fulfill the preceding requirements.

The composition of the present invention may be used for any application in which it is desirable to employ a product that offers protective properties toward metals.

The compositions of the invention, once topically applied on the skin, are used in a cosmetic method for reducing or preventing contact dermatitis, or for reducing allergies to metals.

Alternatively, the composition of the invention is sprayed or coated on clothes or protective personal equipment or object in contact with the skin.

The compositions of the invention are also useful as a medicament.

Preferably, they can be used to reduce or prevent contact dermatitis as well as to prevent allergies to metals.

Moreover, the compositions of the invention are used to reduce undesired effects on skin following to contact with irritating metals.

Another application for these products is their development to protect people toward radioactive elements such as uranium, which people may be exposed in potentially contaminated environments. Some metals such as uranium present radioactive positively charged isotopes that could be captured by the polymers described within this invention. These products could be used as skincare, or deposited on top of clothes or protective gears, or personal protective equipment, or any item containing the metal in the form of a coating layer. The compositions of the invention are therefore useful to limit risks induced by exposure to radioactive material. Preferably, the radioactive element is uranium.

The compositions of the invention are used in a method for reducing risks of undesired effects on skin of contact with metals, whether these contacts come from objects or environmental conditions. They are also useful in a method for reducing risks of undesired effects on health due to contact with radioactive isotopes.

Said compositions can be used for prevention or treatment.

The compositions according to the invention are applied on the skin or cutaneous surface of an individual, on the metal-containing object, on clothes or other material to be protected from metal exposition. Depending on the method of administration, the compositions according to the invention can be in all the forms usually employed in cosmetics or in medications. Said compositions can in particular be formulated as ointments, creams, milks, gels, lotions, sprays, sticks, powders or liquids.

The following examples illustrate the invention without limiting it in any way.

EXAMPLES

Example 1: Evaluation of Protecting Properties of Non Dissociable Polymeric Metal Capturing Agents a) Principle of the Test An in vitro test has been developed. The DMG (dimethylglycoxime) is used to develop a color test revealing the presence of nickel ions, whatever in a solution, a pellet, a solid support or on human skin. This test is developed to estimate the trapping abilities of the cream when exposed to nickel.

Briefly, a solution of nickel is contacted with the composition to be tested. After homogenization and incubation at room temperature, the solution is centrifuged, and the hydrated polymer is collected in the pellets while the polymer free aqueous phase is collected in the supernatant. To test the presence of free nickel ions, 10 µL of the supernatant is collected and deposited on a blot paper. The presence of free nickel is revealed by swabbing a DMG solution with a cotton wood. In presence of nickel, DMG turns pink.

b) Nickel Capture with Carboxyl Moieties

500 µL of a solution of Carbomer Carbopol Ultrez 10 polymer (Lubrizol), at 4% w/w in water into which 50 µL of nickel solution in water (High Purity Standards) has been added, has been incubated for 1 hour at room temperature. The mixture was then centrifuged to separate polymer from the supernatant. 10 µL of supernatant has been deposited on a filter paper and DMG (Chemo nickel Test—Chemotechnique Diagnostics) has been deposited with a swab on this spot. 6 concentrations of nickel have been tested from a stock nickel solution concentration of 1 mg/mL: 500 µg/mL, 250 µg/mL, 125 µg/mL, 62.5 µg/mL, 31.3 µg/mL, 15.6 µg/mL.

To determine the efficiency of the capture, a blank has been made with solutions of nickel in water at the same concentrations. The experiment was performed in three replicates (A, B, C).

Figure 2:
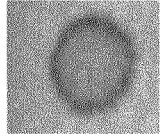
FIG. 2: Nickel in aqueous solutions at various concentrations, revealed by DMG without compositions to be tested. Concentrations of nickel are the same as above.

The results are shown in FIG. 1 for carbomer and FIG. 2 for the blank. The intensity of the color has been determined using ImageJ software (National Institute of Health, USA) as a grey scale. The results are summarized in table 1.

TABLE 1 grey values determined with ImageJ software on the spots revealed by DMG.

| [Ni$^{2+}$] µg/mL | 15.65 | 31.25 | 62.5 | 125 | 250 | 500 |
|---|---|---|---|---|---|---|
| Carbomer 4% | 0 | 0 | 0 | 14 (+/−6) | 22.7 (+/−8.6) | 32.3 (+/−2.9) |
| H2O | 0 | 9.6 (+/−0.6) | 22.3 (+/−2.1) | 28 (+/−8.2) | 41.3 (+/−2.1) | 50 (+/−4.4) |

For all concentrations tested, the grey value intensity of the spot after DMG is lower when the supernatant is tested, compared to aqueous solutions. It means that the carbomer tested is able to capture nickel ions in solution.

c) Nickel Capture with Sulfonyl Moieties

Two compositions were tested toward nickel capture. Detailed description of the compositions is reported in Table 2 below.

| Ingredients | Composition A | Composition B |
|---|---|---|
| Castor oil (Olvea) | 20% | 20% |
| Isononylisononanoate (SEPPIC) | 25% | 25% |
| Emulgade 1000 Ni (BASF) | 5% | 5% |
| Poly (2-acryloamideo-2-methyl-1 propanesulfonic acid) (Sigma Aldrich) | — | 7.5% |
| Water | qsp 100% | qsp 100% |

Briefly, isononyl Isononanoate, castor oil and emulgade 1000 Ni were mixed at 70° C., then added to water at 70° C. (Composition A) or to the water containing the polymer (Composition B) at 70° C. and mixed while let to cool down.

Figure 3:
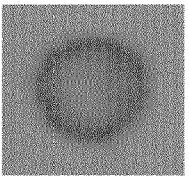
FIG. 3: Spots of nickel detected by DMG in compositions A and B. Each composition was tested twice (Sample 1 and Sample 2), and each sample was tested twice for the detection of nickel (a and b).
Figure 3:
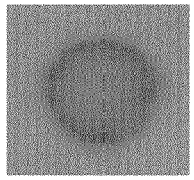
Figure 3:
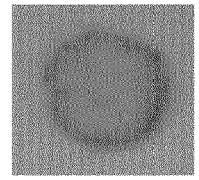
Figure 3:
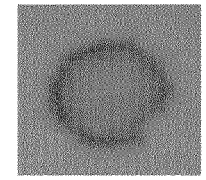
Figure 3:
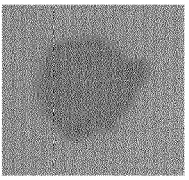
Figure 3:
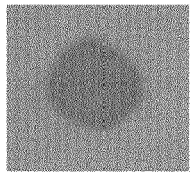
Figure 3:
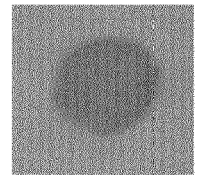
Figure 3:
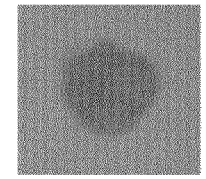
Figure 3:
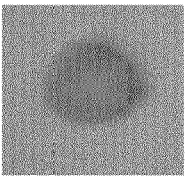
Figure 3:
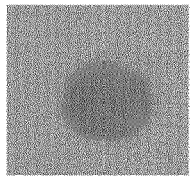
Figure 3:
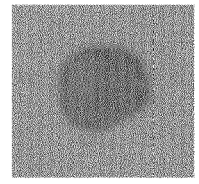
Figure 3:
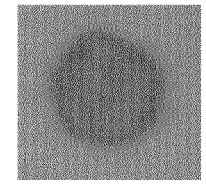
Figure 3:
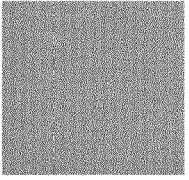
Figure 3:
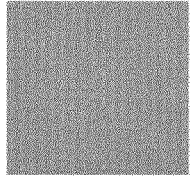
Figure 3:
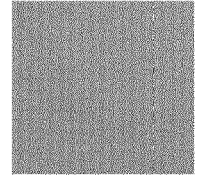
Figure 3:
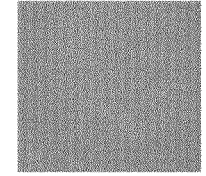

50 µL nickel at 0,125 g/L was added to 500 µL of the compositions A or B, and the mixtures were vortexed and then allowed to rest for 30 minutes before being centrifugated at 13000 rpm for 30 minutes. 10 µL of the supernatant and 10 µL of the pellet for each sample were deposited on a blotter paper sheet and DMG was applied on the spots. The appearance of a pink color reveals the presence of nickel ions in the sample. Experiments were made twice, and two tests (a and b) per sample were made. The results of the detection of nickel ions with DMG in the pellet or supernatant of composition A and B are summarized in Table 3 below and also in FIG. 3.

| Sample | Detection of nickel (% surface coverage pink colored) |
|---|---|
| Formula A pellet | 34% (±5%) |
| Formula A supernatant | 25% (±5%) |
| Formula B Pellet | 20% (±6%) |
| Formula B supernatant | 0% |

Indeed, nickel is detected both in the supernatant and the pellet of a composition containing no sulfonyl moieties bearing polymer, meaning there was no preferential binding of this element in the composition A. On the other hand, the nickel was only detected in the pellet of the composition B containing Poly (2-acryloamideo-2-methyl-1 propanesulfonic acid) (sulfonyl moieties bearing polymer). Nickel is bound to the polymer. The size of nickel/polymer complex is large enough to avoid its penetration into skin, preventing the skin absorption of the nickel ions capture by the polymer.

d) Nickel Capture with Sulfate Moieties

Two compositions were tested toward nickel capture. Detailed description of the compositions is reported in Table 4.

| Ingredients | Composition C | Composition D |
|---|---|---|
| Castor oil (Olvea) | 20% | 20% |
| Isononylisononanoate (SEPPIC) | 25% | 25% |
| Emulgade 1000 Ni (BASF) | 0.5% | 0.5% |
| iota-carrageenan (Aromazone) | — | 10.00% |
| Water | qsp 100% | qsp 100% |

Isononyl Isononanoate, castor oil and emulgade 1000 Ni were mixed at 70° C., then added to water at 70° C. (Composition C) or to the water containing the iota-carrageenan polymer (Composition D) at 70° C. and mixed while let to cool down.

50 µL nickel at 0,125 g/L was added to 500 µL of the compositions A or B. The mixtures were vortexed and then allowed to rest for 30 minutes before being centrifuged at 13000 rpm for 30 minutes. 10 µL of the supernatant and 10 µL of the pellet for each sample were deposited on a blotter paper sheet and DMG was applied on the spots. The appearance of a pink color reveals the presence of nickel ions in the sample. Experiments were made twice, and two tests (a and b) per sample were made.

Figure 4:
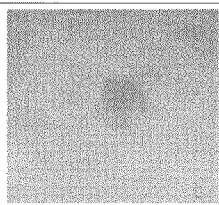
FIG. 4: Spots of nickel detected by DMG in composition C and D. Each composition was tested three times for the detection of nickel (Sample 1, 2, 3).
Figure 4:
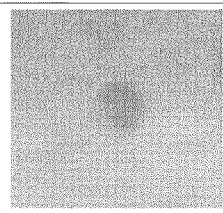
Figure 4:
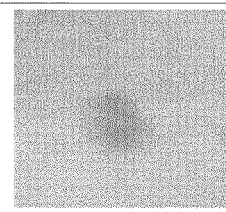
Figure 4:
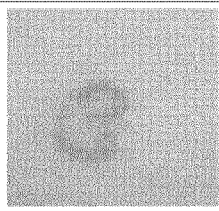
Figure 4:
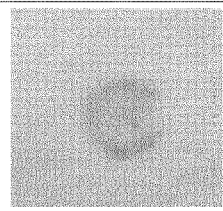
Figure 4:
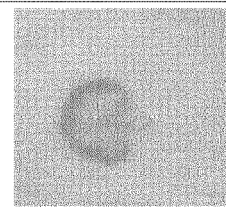
Figure 4:
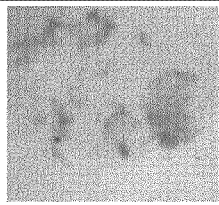
Figure 4:
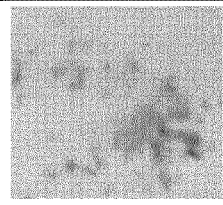
Figure 4:
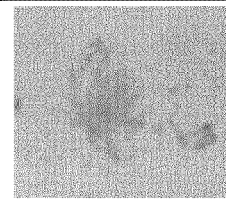
Figure 4:
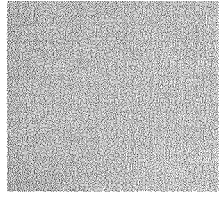
Figure 4:
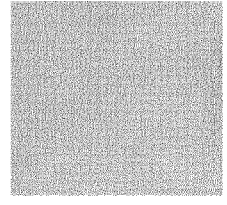
Figure 4:
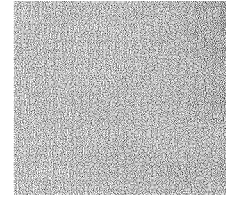

Table 5 and the results of FIG. 4 report the detection of nickel ions with DMG in the pellet or supernatant of compositions C and D. Three tests were made by sample.

| Sample | Detection of nickel (% surface coverage pink colored) |
|---|---|
| Formula C pellet | 11% (±3%) |
| Formula C supernatant | 5% (±2%) |
| Formula D Pellet | 17% (±2%) |
| Formula D supernatant | 0% |

Nickel is detected both in the supernatant and the pellet of a composition containing no sulfate moieties bearing polymer (iota-carrageenan). On the other hand, the nickel was detected only in the pellet of the composition D. Nickel is bound to the polymer. The size of nickel/polymer complex is large enough to avoid its penetration into skin, preventing the skin absorption of the nickel ions capture by the polymer.

Example 2: Nickel Protective Cream with Carbomer

A protective composition as described in Table 6 below is made by adding all the ingredients of phase A in a beaker heated in water bath at 70° C. Then, aqua, glycerin, hexanediol and chlorphenesin are mixed and heated at 70° C. under stirring. Once all the ingredients are dissolved and the mixture is homogeneous, the carbomer is added under light stirring in order to let it hydrate.

Once hydration is completed, Phase A is added in Phase B under strong agitation and the preparation is let slowly cooling down at room temperature. Then, a solution of NaOH at 0.05 M is used to buffer the composition at pH 6.

The protective cream is to be applied at a concentration of 4 mg/cm$^2$.

TABLE 6 detailed composition of a nickel-protective cream.

|  | Ingredients | % Ingredients |
|---|---|---|
| Phase A | Castor Oil | 10.00% |
|  | Emulgade 1000 Ni (BASF) (split in 2) | 5.50% |
|  | LANOL 99 | 15.00% |
|  | Tocopheryl Acetate | 0.10% |
| Phase B | Aqua | Qsp 100% |
|  | Chlorphenesin (Azelis) | 0.30% |
|  | Carbopol Ultrez 10 (Lubrizol) | 4.00% |
|  | Glycerin (Cooper) | 3.00% |
|  | EMOLLIENT Microcare HXD (Thor) | 1.50% |

Example 3: Synergic Effects of Carbomer Together with CaCO3 Particles

Polyacrylic acid polymers known as carbomer have the properties to be acidic in aqueous solutions with the presence of numerous free COOH moieties. The ability of carbomer to bind nickel ion has been tested in an in vitro test according to the following protocol. A carbomer (Carbopol Ultrez 10, Lubrizol) suspension at 0.3% is hydrated in a glycerol/H2O (1/3) solution and tested according to the same protocol as the one described in example 1.

To test the efficiency of the combination of both metal capturing agent, the association of carbomer with CaCO3 has been tested, and a comparison has been made with CaCO3 particles alone. The detailed compositions and their final pH are described in table 7.

| Name | Composition (% of total weight) | Protocol | pH |
|---|---|---|---|
| Composition A | Glycerin 20% CaCO3 20% Water: qsp 100% | mix glycerin and water at 50° C., when homogeneous, add CaCO3 powder under stirring and let cool down at room temperature. | 9.7 |
| Composition B | Glycerin 20% CaCO3 20% Water: qsp 100% HCl 25% qsp pH stabilization | mix glycerin and water at 50° C., when homogeneous, add CaCO3 powder under stirring and let cool down at room temperature. Once at RT, add HCl to stabilize the composition at pH 7 | 7 |
| Composition C | Glycerin 20% CaCO3 20% Water: qsp 100% HCl 25% qsp pH stabilization | mix glycerin and water at 50° C., when homogeneous, add CaCO3 powder under stirring and let cool down at RT. Once it is at room temperature, add HCl to stabilize the composition at pH 5 | 5 |
| Composition D | Glycerin 20% H2O 60% Cabomer 0.3% | mix glycerin and water at 70° C., when homogeneous, add carbomer under stirring and let hydrate. Once hydration complete, let cool down at room temperature. | 3.6 |
| Composition E | Glycerin 20% CaCO3 20% Water: 60% carbomer 0.3% | mix glycerin and water at 70° C., when homogeneous, add carbomer under stirring and let hydrate. When carbomer hydration is completed, add CaCO3 powder under stirring and let cool down at room temperature. | 6.9 |

The grey level of the spots obtained after DMG swabbing has been evaluated using Image J Software. The results are expressed as a function of the control which is a spot of nickel in H2O/glycerol to evaluate the efficiency of the nickel capture of the tested composition.

Figure 5:
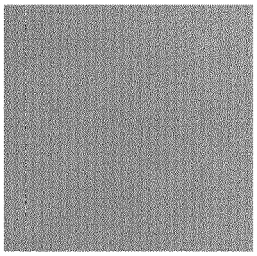
FIG. 5: Spots of nickel detected by DMG in compositions A, B, C, D, E and in a glycerol/water 1/3 solution. Each sample was tested three times (Test 1, Test 2 and Test 3).
Figure 5:
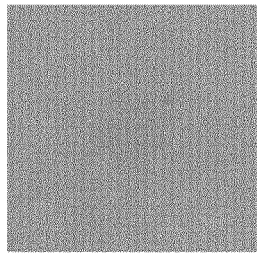
Figure 5:
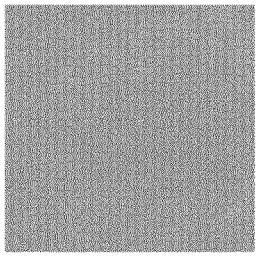
Figure 5:
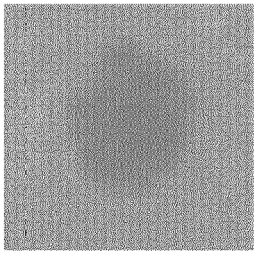
Figure 5:
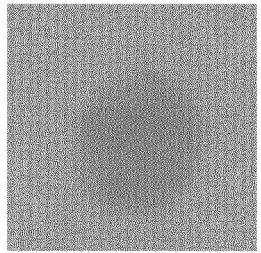
Figure 5:
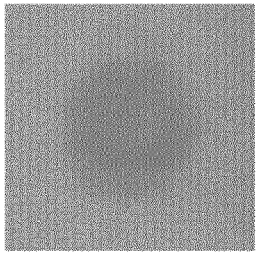
Figure 5:
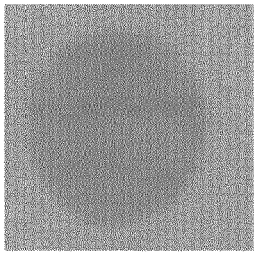
Figure 5:
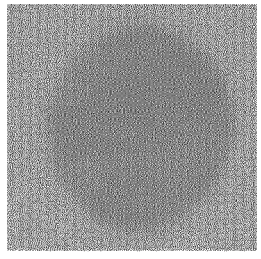
Figure 5:
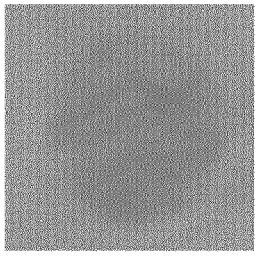
Figure 5:
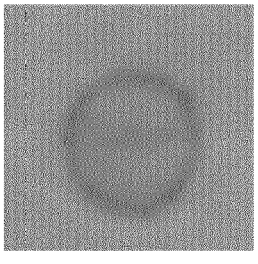
Figure 5:
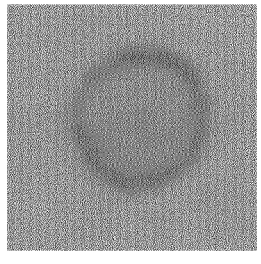
Figure 5:
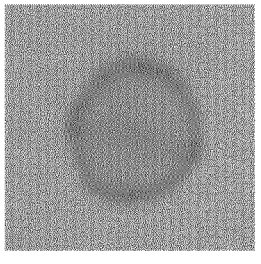
Figure 5:
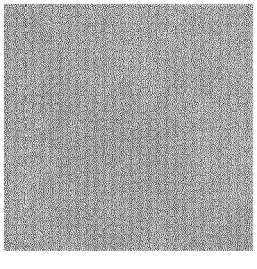
Figure 5:
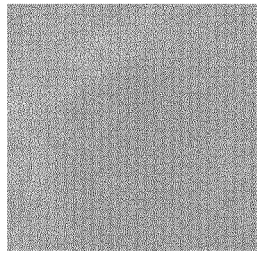
Figure 5:
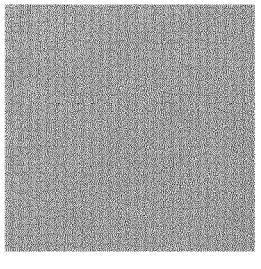

The results are summarized in table 8 below and in FIG. 5.

TABLE 8

Percentage of capture efficiency of 10 µg of nickel by 500 µL of composition A, B, C, D and E.

|  | % of efficiency of capture compared to nickel in H2O/Glycerin |
|---|---|
| Composition A | 100% |
| Composition B | 48% (+/−5%) |
| Composition C | 30% (+/−7%) |
| Composition D | 7% (+/−3%) |
| Composition E | 100% |

Carbomer alone is able to capture nickel as demonstrated in example 2. Even at a concentration as low as 0.3% (composition D), the polymer is able to capture 4 to 10% of nickel added to the suspension. When this polymer is mixed with CaCO3 particles, the mixture has a pH compatible with skincare products. The efficiency of the composition E (Carbomer+CaCO3 particles) is higher than the addition of the efficiency of compositions B and D, showing the synergic effect observed for the presence of both carbomer and CaCO3 particles.

Indeed, the CaCO3 particles alone are able to capture nickel ions in solution. However, the pH of such aqueous composition is too high to be suitable for a cosmetic or pharmaceutical topical product. Decreasing pH to render it acceptable for skin drastically reduces the efficiency of nickel capture (see the results of compositions A and B). This lower efficiency of the CaCO3 particles alone observed at pH compatible with skin is explained by partial solubilization of CaCO3 in acidic pH.

Example 4: Protecting Effects of a Composition with Mineral Metal Capturing Agent, Metal Capturing Polymeric Agent and pH Buffering Agent A composition with CaCO3 buffered with HCl—a common pH adjusting agent—together with alginate has been tested according to the following protocol:

Alginate polymer powder (1%) is hydrated in a glycerin/H2O solution (1/3). After solubilization of the powder, CaCO3 (20% w/w) particles are incorporated. The pH is corrected at 6.5 using an HCl (25%) solution (composition D). To evaluate the efficiency of this composition, the following compositions have been prepared as controls:

Composition A: Glycerin (25%)+H2O (75%)
Composition B: Glycerin (20%)+H2O (60%)+CaCO3 (20%) pH 9.7
Composition C: Glycerin (20%)+H2O (60%)+CaCO3 (20%)+HCl pH 5

100 µL of each of these compositions has been coated on top of a polycarbonate membrane with pores diameter of 30 nm (Avanti Polar Lipids) and the coated membranes have been deposited on top of a filter paper. 10 µL of a nickel solution at 68 µL/mL has been deposited on the center of these coated membrane and let to interact for 5 to 10 minutes.

Figure 6:
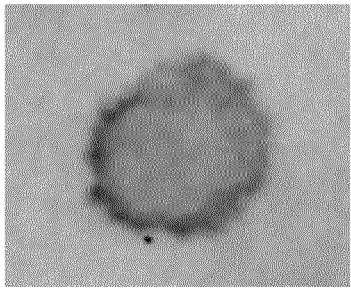
FIG. 6: Spots of nickel detected by DMG in compositions A, B, C and D after 10 µL of nickel solution has been deposited on top of polycarbonate membranes coated with each composition and let to absorb on an underlying filter paper.
Figure 6:
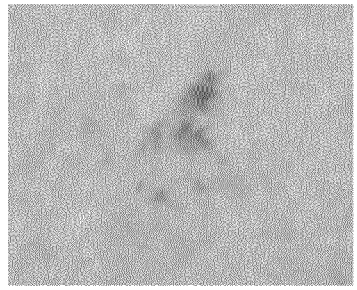
Figure 6:
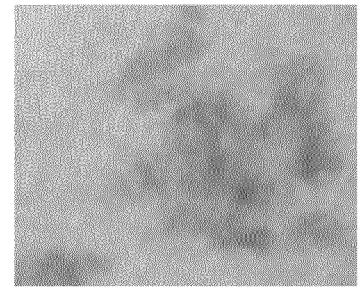
Figure 6:
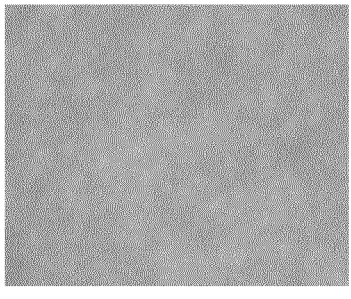

After this time, the membranes were removed and a DMG soaked swab has been used to reveal nickel presence on the underlying filter paper. To estimate the efficiency of nickel capture, the percentage of pink surface area colored after swabbing with DMG is reported. Results are summarized in table 9 and in FIG. 6.

TABLE 9 percentage of surface area that turned pink after coating with DMG, once the nickel solution has been deposited on top of a polycarbonate filter.

|  | % of surface area which has reacted with DMG |
| --- | --- |
| Composition A | 35% |
| Composition B | 4% |
| Composition C | 47% |
| Composition D | 0% |

The glycerin/H2O solution (composition A) allowed nickel ions to strongly cross the polycarbonate membrane.

With glycerin+H2O+carbonate (composition B or C), the intensity of the spot depends on the pH of the composition (very weak for 9.7, stronger for pH 5). This is coherent with the results of example 3.

Finally, no detection of nickel was observed for composition with CaCO3 buffered with HCl, together with alginate (composition D). This demonstrates that, at a pH compatible with skincare products, a composition containing a metal capturing agent that does not cross the skin like alginate is very efficient when combined with CaCO3 particles showing quite a low efficiency at a pH compatible with skincare products.

The invention claimed is:

1. A topical composition to protect skin against contact with metal irritants and allergens that comprises, at least one metal capturing agent bearing carboxyl moieties, and further comprising from 10% to 25% of the total weight of the composition of an agent chosen among zeolite, hydroxyapatite, calcium carbonate, calcium phosphate, ammonium calcium silicate, microporous aluminosilicate, sodium aluminosilicate, calcium silicate, sodium calcium aluminosilicate, and magnesium carbonates, tricalcium silicate, magnesium phosphate, manganese carbonate;
wherein the carboxyl bearing agent is a carbomer, present in an amount ranging from 0.1 to 10% of the total weight of the composition, and
wherein the topical composition has a pH of from 4 to 8.

2. A topical composition according to claim 1, wherein the metal irritant or allergens is a metal cation.

3. A topical composition according to claim 1, wherein the metal irritant or allergen is nickel, cobalt, chromium, zinc or lead.

4. A topical composition according to claim 1, as a medicament.

5. A topical composition according to claim 1 for its use to reduce or prevent contact dermatitis.

6. A topical composition according to claim 1 for its use to prevent allergies to metals.

7. A topical composition according to claim 1 for its use to reduce undesired effects on skin following to contact with irritating metals.

8. A topical composition according to claim 1 for its use to limit risks induced by exposure to radioactive material.

9. A topical composition according to claim 8, wherein the radioactive material is uranium.

10. A topical composition according to claim 1, wherein the composition has a physiological pH.

11. A topical composition according to claim 1, wherein the composition has a pH of from 5.5 to 6.9.

* * * * *